United States Patent
Goode et al.

(10) Patent No.: US 10,278,803 B2
(45) Date of Patent: May 7, 2019

(54) VENA CAVA FILTER REMOVAL DEVICE

(71) Applicant: Cook Medical Technologies LLC, Bloomington, IN (US)

(72) Inventors: Louis B. Goode, Cranberry Township, PA (US); Maureen A. Secilia, Kittanning, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 359 days.

(21) Appl. No.: 14/203,725

(22) Filed: Mar. 11, 2014

(65) Prior Publication Data

US 2014/0277089 A1    Sep. 18, 2014

Related U.S. Application Data

(60) Provisional application No. 61/776,842, filed on Mar. 12, 2013.

(51) Int. Cl.
*A61F 2/01* (2006.01)
*A61B 17/00* (2006.01)

(52) U.S. Cl.
CPC ...... *A61F 2/01* (2013.01); *A61B 2017/00358* (2013.01); *A61F 2002/011* (2013.01)

(58) Field of Classification Search
CPC .............. A61F 2/01; A61F 2002/011; A61F 2002/9528; A61F 2002/9534; A61B 17/221; A61B 2017/00358; A61B 2017/2212; A61B 17/32056
See application file for complete search history.

(56) References Cited

U.S. PATENT DOCUMENTS

| 5,171,233 A | 12/1992 | Amplatz et al. |
| 5,171,314 A | 12/1992 | Dulebohn |
| 5,324,304 A | 6/1994 | Rasmussen |
| 5,370,657 A | 12/1994 | Irie |
| 5,413,586 A | 5/1995 | Dibie et al. |

(Continued)

FOREIGN PATENT DOCUMENTS

| JP | 2003-503085 A | 1/2003 |
| JP | 2011-083626 A | 4/2011 |

(Continued)

OTHER PUBLICATIONS

Cook Medical, "Gunther Tulip Vena Cava Filter Retrieval Set for Jugular Vein Approach, Instructions for Use Optional Retrieval Procedure", May 2008, 1-9 pp.

(Continued)

*Primary Examiner* — Ryan J. Severson
*Assistant Examiner* — Christian D Knauss
(74) *Attorney, Agent, or Firm* — Woodard, Emhardt, Henry, Reeves & Wagner, LLP

(57) ABSTRACT

A vascular filter retrieval device and methods of using the same are disclosed. In particular, some embodiments disclose a vascular filter retrieval device having a strut engaging member coupled to a loop. A retrieval device with an elongate member coupling a strut engaging member and loop are also disclosed. The present disclosure also provides a device having an orienting member arranged to extend at least partially around a vascular filter and orient a strut engaging member with a portion of the vascular filter. Other embodiments are disclosed.

20 Claims, 7 Drawing Sheets

(56) References Cited

U.S. PATENT DOCUMENTS

| | | | |
|---|---|---|---|
| 5,626,605 A | 5/1997 | Irie et al. | |
| 5,993,474 A | 11/1999 | Ouchi | |
| 6,106,532 A * | 8/2000 | Koike | A61B 17/0057 606/138 |
| 6,123,665 A * | 9/2000 | Kawano | A61B 17/3478 600/104 |
| 6,342,062 B1 | 1/2002 | Suon et al. | |
| 6,342,063 B1 | 1/2002 | DeVries et al. | |
| 7,530,983 B1 * | 5/2009 | Jenkins | A61B 17/32056 606/110 |
| 7,625,390 B2 | 12/2009 | Hendriksen et al. | |
| 7,763,045 B2 | 7/2010 | Osborne | |
| 2001/0000348 A1 * | 4/2001 | Chu | A61B 17/221 606/113 |
| 2002/0198536 A1 * | 12/2002 | Trout, III | A61B 17/064 606/138 |
| 2003/0071285 A1 | 4/2003 | Tsukernik | |
| 2005/0119668 A1 * | 6/2005 | Teague | A61B 17/221 606/127 |
| 2005/0209609 A1 * | 9/2005 | Wallace | A61B 17/221 606/113 |
| 2006/0052797 A1 * | 3/2006 | Kanamaru | A61B 17/22 606/113 |
| 2008/0009883 A1 * | 1/2008 | Bieneman | A61B 17/221 606/113 |
| 2009/0118760 A1 | 5/2009 | Clausen et al. | |
| 2009/0182370 A1 | 7/2009 | Vologuyev et al. | |
| 2010/0016875 A1 * | 1/2010 | Nakao | A61B 17/221 606/159 |
| 2011/0040321 A1 | 2/2011 | Cartier et al. | |
| 2011/0295306 A1 | 12/2011 | Blatter | |

FOREIGN PATENT DOCUMENTS

| | | |
|---|---|---|
| WO | WO 00/16846 A1 | 3/2000 |
| WO | WO 03/022325 A2 | 3/2003 |
| WO | WO 2011/043900 A1 | 4/2011 |
| WO | WO 2012/003369 A2 | 1/2012 |

OTHER PUBLICATIONS

English Abstract of JP 2003503085 (Original Japanese document not found).
English Abstract of JP 2011083626.

* cited by examiner

VENA CAVA FILTER REMOVAL DEVICE

REFERENCE TO RELATED APPLICATION

This application claims the benefit of U.S. Provisional Patent Application No. 61/776,842, filed Mar. 12, 2013, which is hereby incorporated by reference in its entirety.

FIELD OF THE INVENTION

The present invention relates to vascular filter retrieval devices and to methods for retrieving vascular filters implanted in patients, and particularly to the retrieval of filters from the vena cava.

BACKGROUND

Vascular filters are used for effective filtration of blood particularly in the inferior vena cava in order to prevent pulmonary thromboembolism. A need for these filters arises in trauma patients, orthopedic surgery patients, neurosurgery patients, or in patients having medical conditions requiring bed rest or non-movement, as these medical conditions present a possibility of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. However, designs for removable filters have been provided, such as U.S. Pat. No. 7,763,045 to Osborne and U.S. Pat. No. 7,625,390 to Hendriksen et al.

Filters typically have a conical design provided with a hook on a top surface for accurate placement in the vena cava. A filter is introduced into a patient using a standard percutaneous technique. If a patient's risk of thromboembolism diminishes, the patient no longer requires a filter and the filter can be removed.

A known retrieval device comprises a snare, shaped as a loop, which is used to catch a removal hook on the top of the filter. Unfortunately, filters can become off-centered or tilted with respect to the hub of the filter and the longitudinal axis of the vessel in which it has been inserted, resulting in the removal hook lying close to or against the vessel wall. This can make snaring the removal hook with a retrieval device difficult if not impossible. Additionally, in the event of this occurrence, there is a greater likelihood of endotheliosis of the filter to the blood vessel along a substantial length of the filter wire and/or the retrieval hook. As a result, the filter can become a permanent implant in a shorter time period than otherwise. It is also possible that, in some patients, the hook on the filter becomes calcified, thus inhibiting retrieval of the filter. Thus, there is a need for alternative devices and methods for retrieving vascular filters implanted in patients.

SUMMARY

In some aspects, the present disclosure describes devices and methods for retrieving vascular filters. In accordance with some embodiments, a retrieval device is configured to engage the struts of an implanted vascular filter so as to allow a catheter to be advanced over at least a portion of the filter and/or collapse the legs of the filter. In some arrangements, the present disclosure teaches a device for retrieving a vascular filter having a plurality of struts from the body of a patient, comprising a catheter defining a lumen; a loop deployable from and retractable into the lumen; and a strut engaging member coupled to the loop and defining first and second strut receiving recesses each arranged to receive at least one strut of the vascular filter. In some instances, the loop is self-opening and/or can be arranged to position the strut engaging member between struts of the vascular filter. Additionally or alternatively, the loop can be arranged to surround the vascular filter. In some arrangements, the strut receiving recesses are defined by a plurality of elongate outward protrusions on the strut engaging member.

In some embodiments, a device for retrieving a vascular filter having a plurality of struts from the body of a patient comprises a catheter defining a lumen; a loop deployable from and retractable into the lumen; and an elongate member coupling a strut engaging member to the loop. In some instances, the elongate member can be wrappable around at least one strut of the vascular filter. Alternatively or additionally, the strut engaging member can be arranged to hook the elongate member, such as after the elongate member has been wrapped around one or more struts of the vascular filter.

In some arrangements, the present disclosure describes a device for retrieving a vascular filter having a plurality of struts from the body of a patient, comprising an orientating member having a strut engaging member coupled thereto; the orientating member arranged to contact the vascular filter along at least a plurality of discrete points and orient the strut engaging member for engagement with at least one strut of the vascular filter; and the strut engaging member arranged to engage at least one strut of the vascular filter and couple at least a portion of the orienting member to the vascular filter. In some embodiments, the strut engaging member defines a strut receiving recess arranged to receive at least one strut of the vascular filter, which, in some arrangements, is defined at least in-part by an elongate outward protrusion on the strut engaging member. In some instances, the orienting member comprises a self-opening loop. Additionally or alternatively, the device may further comprise an elongate member coupling the strut engaging member to the orientating member.

The strut receiving recesses discussed herein can be a variety of sizes and shape and can be defined by one or more surfaces of the strut engaging member, the orienting member, and/or the loop. Preferably, the strut receiving recesses are sized larger than the maximum outer dimension of the struts of the vascular filter so that one or more struts of the vascular filter can be caught or received in the strut receiving recess. For example, one or more or each strut receiving recess can be arranged to receive one strut or more than one strut. As will be appreciated by those of ordinary skill in the art, struts of the vascular filter may substantially fill a strut receiving recess within which it is received.

Additionally, in some embodiments, the strut receiving recesses are shaped so as to retain a strut within the strut receiving recess. In some instances, the strut receiving recesses are shaped to mate with portions of the struts. For example, for vena cava filters with struts formed from wire having a round cross-section with a diameter of about 0.015 inches, strut receiving recesses may also have a round-cross section with a diameter of about 0.015 inches or larger. Of course, other cross-sectional shapes are contemplated, such as square or triangular strut receiving recesses to name just a few non-limiting examples. For embodiments with strut receiving recesses, such as those embodiments with protrusions and/or flanges that define strut receiving recesses, portions of the strut engaging member may be arranged so as to form strut receiving recesses with a plurality of acute angles.

As mentioned above, a strut receiving recess may be defined by one or more surfaces of the strut engaging member, the orienting member, and/or the loop. For example, an outer surface of the strut engaging member may define a strut-receiving recess such as a groove or channel in the strut engaging member. Alternatively, a protrusion extending from a surface of the strut-engaging member, the orienting member, and/or the loop may have an outer surface that defines a portion of a strut receiving recess. Preferably one or more surfaces defining the strut receiving recess are open recesses (i.e., not closed) and are arranged to contact a received strut and resist movement of the strut in one or more directions.

In many instances, surfaces defining the strut receiving recess are arranged to contact different portions and/or surfaces of a received strut. For example, a first surface and a second surface defining a strut receiving recess can be arranged to contact a first surface and a second surface of a strut. In some embodiments, surfaces defining a strut receiving recess are positioned opposite one another and/or are arranged to contact opposing portions and/or surfaces of a strut or group of two or more struts. For example, first and second surfaces defining a strut receiving recess may be arranged to contact first and second surfaces of a strut of a vascular filter, wherein the first and second surface of the strut are diametrically opposed to one another.

As the strut receiving recesses may have any number of shapes, the surfaces defining a strut receiving recess may have any number of shapes and may be oriented relative to one another and/or intersect at any number of angles. For example, a surface defining at least a portion of the periphery of a strut receiving recess maybe comprise a planar portion and/or a curvilinear portion. In some instances, a first surface and a second surface defining a strut receiving recess may be offset from one another and parallel. Alternatively, the first and second surfaces defining a strut receiving recess may be transverse to one another. In many instances, one or more of the surfaces defining a strut receiving recess are transverse to an outer surface of the strut engaging member, orienting member, and/or loop. For instances, protrusions from an outer surface of a strut engaging member may include surfaces that extend laterally away from an outer surface of the strut engaging member. In some instances, a surface defining a strut receiving recess may extend radially away from the center of the strut engaging member, orienting member, and/or loop. Additionally or alternatively, a surface defining a strut receiving recess may extend orthogonally from an outer surface of the strut engaging member, orienting member, and/or loop.

Protrusions discussed in the present disclosure that define at least one strut receiving recess can be of a variety of shapes and sizes. Protrusions can be elongate, extend in an outwardly direction, and/or can be straight or curved. In some instances, protrusions comprise a free terminal end and/or are cantileveredly supported from one end. In some embodiments, one or more or all of the protrusions comprise spikes and can, if desired, comprise a sharp tip. Protrusions can have a various cross-sectional shapes, such as a circular shape cross-sectional shape or a triangular cross-sectional shape, just to name a few non-limiting examples. In some instances, elongate protrusions can vary in size and/or shape along their length. For example, the portion of a protrusion extending from a central portion may have a first cross-sectional shape with the free terminal end of the protrusion having a second cross-sectional shape. Similarly, elongate protrusions can have bends and twists in various directions and may comprise one or more straight and/or curved sections.

In some instances, protrusions resemble barbs and can be positioned relative to one another so as to resemble a fish hook and/or grappling hook configuration (e.g., a treble-hook). Additionally or alternatively, protrusions can be positioned on one or more sides of a central portion of a strut engaging member, an orienting member, and/or a loop.

The strut engaging member, loop, and/or an elongate member may be coupled to one another by any means apparent to those of ordinary skill in the art, such as laser welding, brazing, or crimping. Alternatively, one or more of these members may be integrally formed with another member. For example, the strut engaging member may be integrally formed with an elongate member that is coupled to the loop by laser welding or by a knot (e.g., tying the elongate member around the loop).

In some instances, the device comprises an orienting member arranged to position a portion of the device in a desired relationship with the implanted vascular filter. For example, the orienting member may be arranged so as to position the strut engaging member between adjacent struts of the vascular filter so that a portion of the strut engaging member, such as a strut receiving recess, will engage one or more struts of the vascular filter and couple the filter and retrieving device. Alternatively or additionally, the orienting member can be arranged to orient one or more catheters with the vascular filter.

An orienting member may be arranged to form any of a variety of geometrical shapes and, in some instances, may be configured for particular filters. For example, the orienting member may be arranged to have one or more corners each arranged to receive individual legs of the vascular filter. As one specific example, the orienting member may be in the shape of an octagon. Alternatively or additionally, the orienting member can be arranged to have portions that index to the spaces between the struts of the vascular filter, such as angled portions extending inwards towards the center of the filter when aligned with a gap between adjacent struts of the filter.

In some embodiments, orienting member extends along a portion of the periphery of an implanted filter when in position. However, in some instances, orienting member substantially surrounds the implanted filter when in position. For example, an orienting member may extend around the struts of the vascular filter.

One or more visualizable markers may be positioned on or in one or more of the portions of the device. Preferably, the visualizable markers are visualizable after the retrieval device has been positioned within the body of a patient. For example, catheter 102 disclosed herein may have one or more radiopaque markers to indicate the distal portion of the device. Similarly, radiopaque and/or ultrasonically detectable markers may be positioned on or in portions along the length of loop 120 so that one may visualize the deployment, retraction, and/or positioning of loop 120 within the body of a patient.

As will be appreciated, any material apparent to be suitable by those of ordinary skill in the art may be used to form the devices described herein. For example, strut engaging members may be formed from a material such as stainless steel, titanium, platinum, or nitinol just to name a few non-limiting examples. Similarly, catheters disclosed herein may be constructed of known materials such as nylon and/or a nylon wrapped stainless-steel braid. Loop, such as loop 120 disclosed herein, may be comprised of a metal alloy, for example, a Cobalt-Chromium-Nickel alloy such as ELGILOY® (also known as phynox), Nitinol, or braided Platinum, just to name a few non-limiting examples. The typical chemical composition of the ELGILOY® alloy is 39-41% Cobalt, 19-21% Chromium, 14-16% Nickel, 11-21% Iron, 6-8% Molybdenum, and 1-3% Manganese. Advantageously, materials like ELGILOY®, manufactured by Combined Metals of Chicago LLC, can give a combination of high strength, ductility, and good mechanical properties as well as excellent fatigue life and corrosion resistance.

It should be appreciated, that concepts and features illustrated and/or described in some embodiments are not intended to be limited to only those embodiments, unless otherwise stated. In other words, it is contemplated that features described with some embodiments may be substituted for or combined with features illustrated in other embodiments. Similarly, the illustrated and described embodiments are not intended to be limited to only the combination of features illustrated.

Further forms, objects, features, aspects, benefits, advantages, and embodiments of the present invention will become apparent from a detailed description and drawings provided herewith.

DESCRIPTION OF THE ILLUSTRATED EMBODIMENTS

Figure 1:
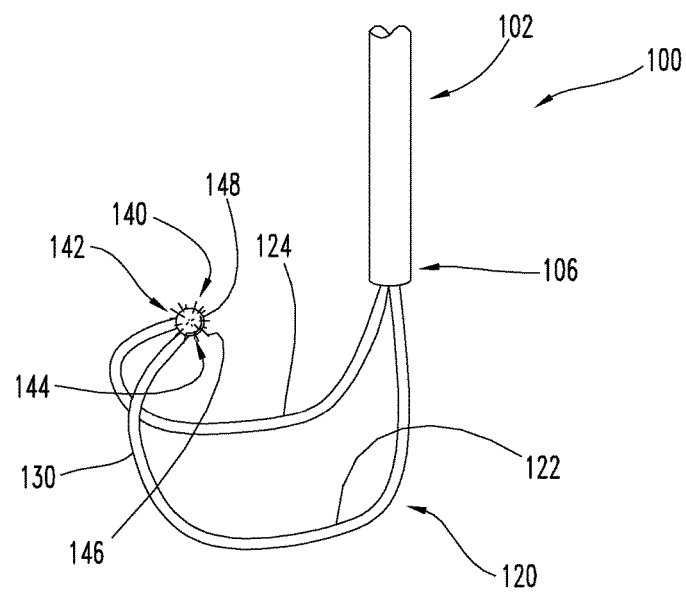
FIG. 1 is a perspective view of one embodiment of a retrieval device.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

Figure 2:
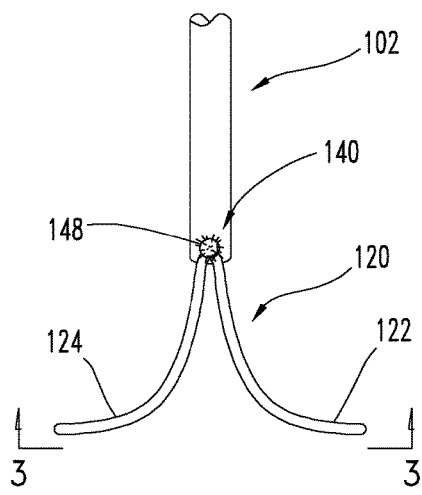
FIG. 2 is a front elevational view of the embodiment illustrated in FIG. 1
Figure 3:
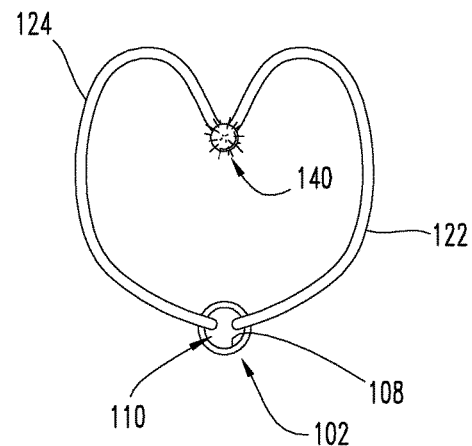
FIG. 3 is a bottom view of the embodiment illustrated in FIGS. 1 and 2.

FIGS. 1, 2, and 3 illustrate a device 100 for retrieving from the body of a patient a vascular filter having a plurality of struts. The device 100 comprises a catheter 102 having a proximal end (not shown) and a distal end 106. Catheter 102 has an inner surface 108 that defines a lumen 110 arranged to receive a portion of a deployable and/or retractable member and/or a portion of the vascular filter being retrieved.

In some instances, the deployable and/or retractable member can be a loop 120 comprising a first portion 122 and a second portion 124 arranged to spread into an open configuration as loop 120 is extended from catheter 102. In some instances, the deployable and/or retractable member can be self-expanding and/or self-opening. For example, loop 120 may comprise a spring wire 130 so that, as loop 120 is extended from lumen 110, loop 120 self-opens into an open configuration.

Coupled to a portion of loop 120 is a strut-engaging member 140 defining recesses 142, 144 arranged to receive struts of a vascular filter deployed within the body of a patient. In some instances, strut-engaging member 140 comprises one or more protrusions 146 extending from a central portion 148. Protrusions 146 have surfaces extending transverse to the outer surface of central portion 148 that define the strut-receiving recesses 142, 144.

Figure 4A:
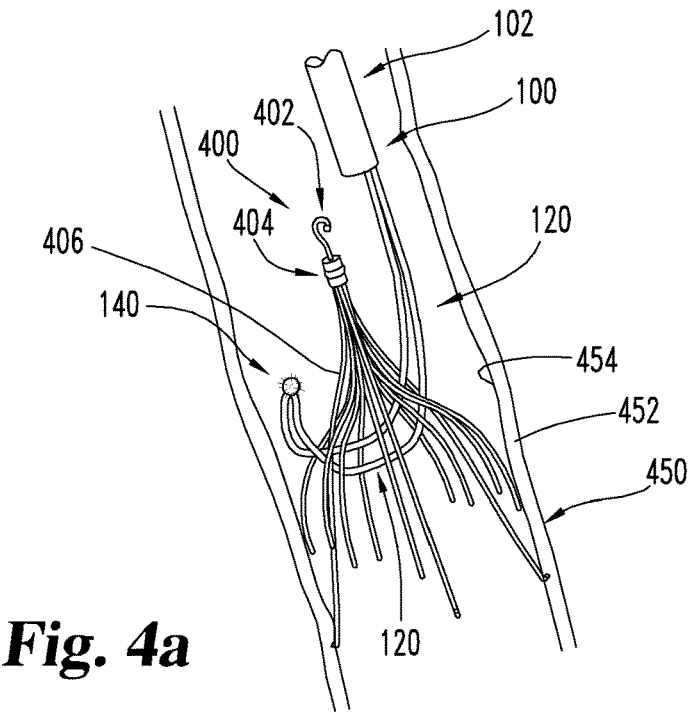
FIGS. 4a and 4b illustrate one method of using an exemplary retrieval device to retrieve an implanted vascular filter.
Figure 4B:
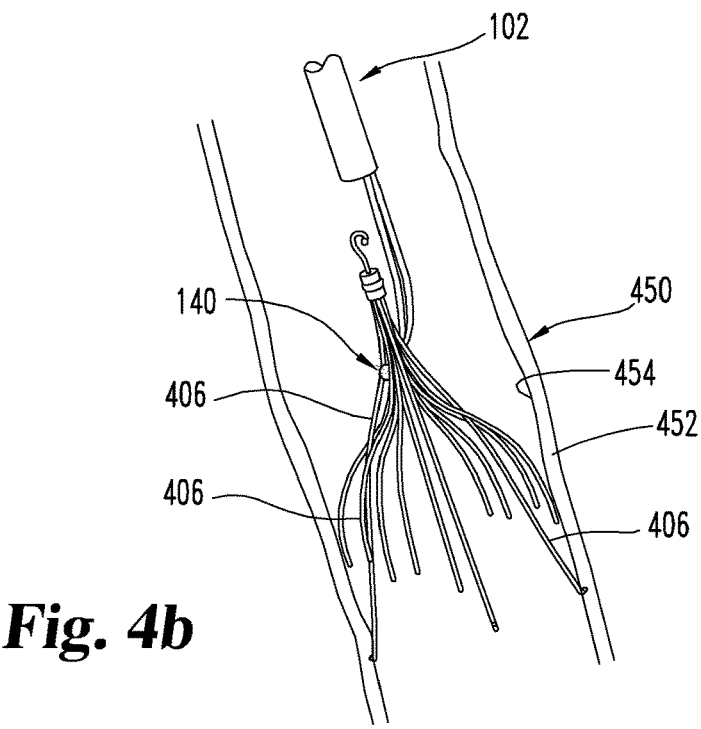

FIGS. 4a and 4b illustrate one exemplary method of using a device for retrieving a vascular filter, such as vascular filter 400, deployed within the vasculature of a patient. Vascular filter 400 illustrated in FIGS. 4a and 4b comprises a removal hook 402 connected by a hub 404 to struts 406. In many instances, a vascular filter, such as vascular filter 400, is implanted in the vena cava for the purpose of lysing or capturing thrombi carried by the blood flowing through the femoral veins toward the heart and into the pulmonary arteries, to prevent the possibility of a pulmonary embolism. When vascular filter 400 is deployed within a vessel 450 of a patient, struts 406 contact vessel wall 452 along inner surface 454. In some instances, struts 406 have barbs that function to retain the vascular filter 400 in the location of deployment. In some embodiments, the barbs puncture vessel wall 452 and anchor the filter at the location of deployment.

To retrieve vascular filter 400, a distal portion of a retrieval device 100 may be advanced towards struts 406 from the side of removal hook 402 and/or hub 404. Loop 120 may then be deployed from within lumen 110 of catheter 102 so that first and second portions 122, 124 of loop 120 spread into an open configuration beneath the hub and/or within the area defined by struts 406 of vascular filter 400 and the portion of loop 120 coupled to strut-engaging member 140 extends between struts 406 of the vascular filter. Device 100 and/or portions thereof such as loop 120 may then be withdrawn in an upward direction, away from struts 406, so as to withdraw strut-engaging member 140 in an upwards direction. As strut-engaging member 140 moves upwards towards hub 404, the size of the openings between struts 406 decrease and a portion of strut-engaging member 140 engages struts 406 of vascular filter 400. As the loop continues to pull strut-engaging member 140 upwards, struts 406 are received within strut receiving recesses 142, 144 and/or portions of strut-engaging member 140 and/or loop may become wedged between struts 406 of the vascular filter 400.

Advantageously, when strut-engaging member 140 and/or loop 120 is engaged with and/or wedged between struts 406 of vascular filter 400, slight tension can be applied to loop 120 so as to align a catheter, such as catheter 102, with vascular filter. Catheter 102 or another catheter positioned around catheter 102 may then be advanced in a downward direction over removal hook 402, hub 404, and/or portions of struts 406 of vascular filter 400. For example, catheter 102 may be advanced over vascular filter 400 so that removal hook 402, hub 404, and portions of struts 406 are received within lumen 110.

In some instances, the strut-engaging member, such as the strut-engaging member illustrated in the above embodiment or the strut-engaging member of other embodiments, is arranged to become wedged between adjacent struts of a vascular filter. However, it should be appreciated that the strut-engaging member may be arranged for engagement of and/or positioning between non-adjacent struts of the vascular filter. For example, the strut-engaging member may be sufficiently sized so that it contacts struts on opposing portions or sides of the vascular filter when the strut-engaging member is positioned beneath the hub and within the area defined by the struts of the vascular filter.

Figure 5A:
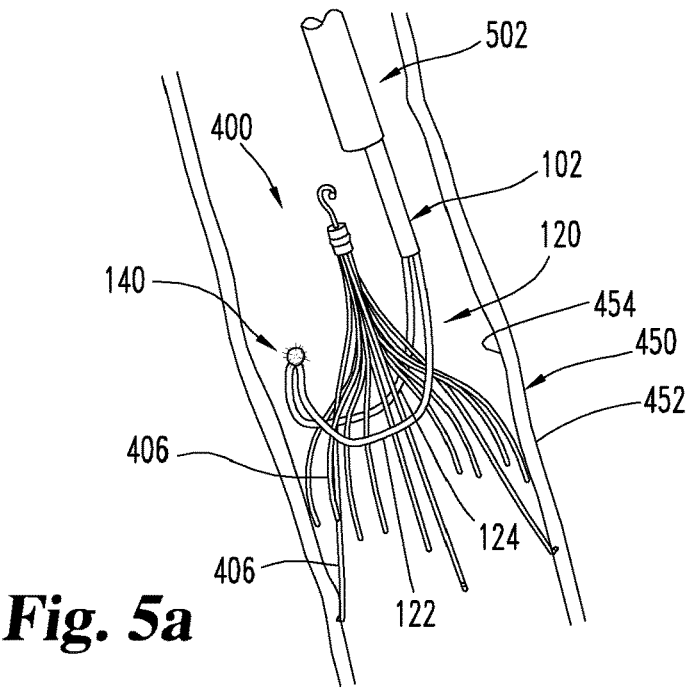
FIGS. 5a and 5b illustrate another method of using an exemplary retrieval device to retrieve an implanted vascular filter.
Figure 5B:
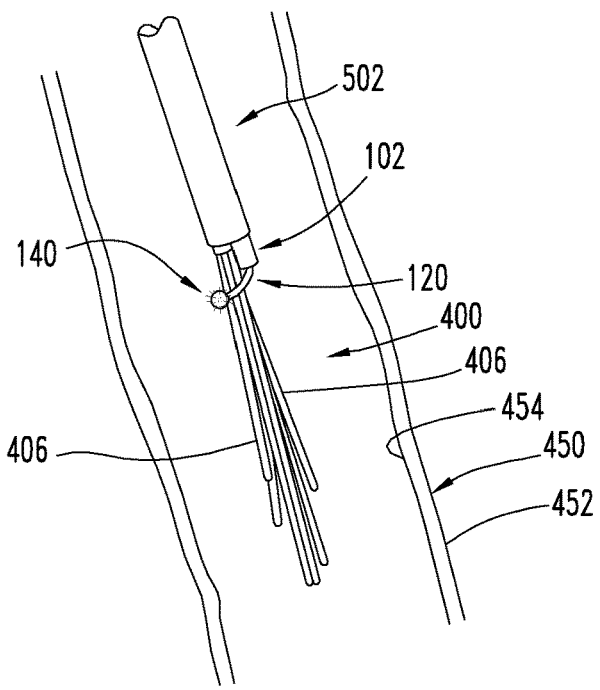

FIGS. 5a and 5b illustrate an alternative method of using the retrieval device, such as device 100, for retrieving a vascular filter. As illustrated in FIG. 5a, loop 120 may be extended from lumen 110 of catheter 102 so as to deploy loop 120 into an open configuration with first and second portions 122, 124 spread apart. Loop 120 may be advanced over removal hook 402, hub 404, and then struts 406 of vascular filter 400 so as to position portions of loop 120, such as first and second portions 122, 124 around struts 406 of vascular filter 400. Catheter 102 may be advanced over loop 120 and/or loop 120 withdrawn into lumen 110 of catheter 102 so as to cinch first and second portions 122, 124 of loop 120 around struts 406.

In some instances, struts 406 can be gathered towards each other and/or removed from vessel wall 452 by closing loop 120. Alternatively or additionally, struts 406 can be gathered by advancing an outer catheter 502 over vascular filter 400. Advantageously, in some instances, the closing of loop 120 around struts 406 can orient catheter 102 with filter 400 so as to facilitate advancement of outer catheter 502 over catheter 102 and portions of filter 400. As portions of vascular filter 400 are received within a lumen of outer catheter 502, struts 406 are collected together and vascular filter 400 is configured into a collapsed configuration, illustrated in FIG. 5b.

During removal of a vascular filter using the methods illustrated in FIGS. 4a, 4b, 5a and 5b, strut-engaging member 140 engages struts 406 and provides traction between loop 120 and portions of vascular filter 400. This arrangement can allow a catheter, such as outer catheter 502, to be advanced over vascular filter 400, such as to gather struts 406, without moving vascular filter 400 through vessel 450, which, advantageously, can reduce trauma caused to vessel wall 452 by preventing the sliding of portions of vascular filter 400, such as barbs, along inner surface 454 of vessel wall 452.

In some instances device 100 comprises a portion arranged to orient and/or position a portion of the device in a desired relationship with the implanted vascular filter. For example, loop 120 may be arranged to orient or position the strut engaging member between adjacent struts of the vascular filter so that a portion of the strut engaging member, such as a strut receiving recess, will engage one or more struts of the vascular filter and couple the filter and retrieving device. Alternatively or additionally, loop 120 can be arranged to orient one or more catheters with the vascular filter.

Figure 6:
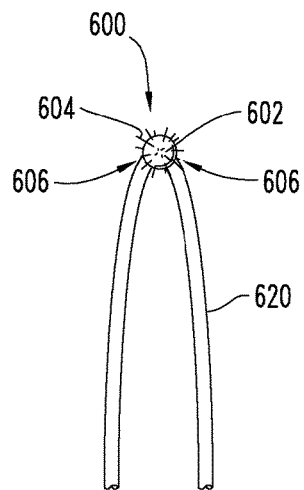
FIG. 6 is a front view of a one embodiment of a strut engaging member.
Figure 7:
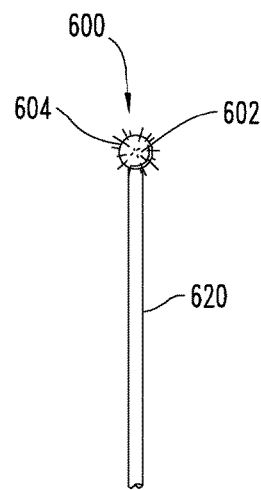
FIG. 7 is a side of the embodiment of FIG. 6.

FIGS. 6 and 7 illustrate one embodiment of a strut engaging member 600 comprising a central portion 602 mounted on a wire 620. In some instances, central portion 602 has protrusions 604 extending therefrom and defining strut receiving recesses 606 therebetween and/or between protrusions 604 and wire 620. As can be seen in FIGS. 6 and 7, central portion 602 may comprise a spherical member, or any other geometrically-shaped member arranged to spread protrusions 604 apart from one another and/or change the directions along which protrusions 604 extend. Central portion 602 illustrated in FIGS. 6 and 7 is centered on wire 620; however, in some instances, central portion 602 resides substantially on one side of wire 620 (e.g., side of wire 620 facing towards loop or side of wire 620 facing away from loop).

Figure 8:
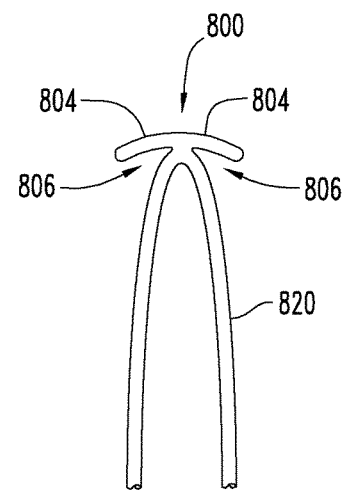
FIG. 8 is a front elevational view of another embodiment of a strut engaging member.

FIG. 8 illustrates another embodiment of a strut-engaging member 800. In this embodiment, strut-engaging member 800 has protrusions 804 that extend substantially in-plane with the portions of wire 820 supporting strut-engaging member 800 (as shown). In this instance, protrusions 804 extend away from wire 820 so as to form strut receiving recesses 806 between protrusions 804 and wire 820. In some embodiments, strut-engaging member 800 and/or portions thereof, such as protrusions 804 can be integrally formed with wire 820.

Figure 9:
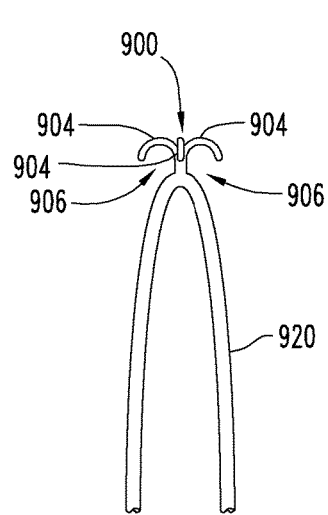
FIG. 9 is a front elevational view of another embodiment of a strut engaging member.

FIG. 9 illustrates an embodiment of a strut engaging member 900 in which protrusions 904 extend away from wire 920 in multiple directions in and/or out of plane with adjacent portions of wire 920. Similar to previously disclosed embodiments, protrusions 904 can be arranged so as to form strut receiving recesses 906 therebetween and/or between one or more protrusions 904 and wire 920.

Figure 10:
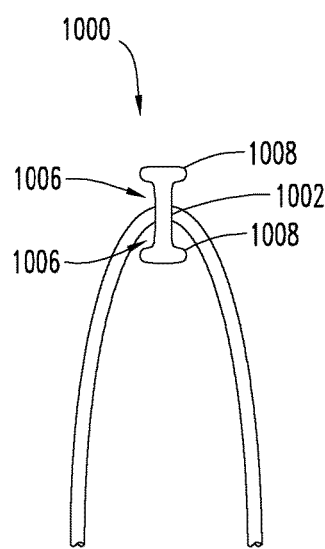
FIG. 10 is a front elevational view of another embodiment of a strut engaging member.

Another embodiment of strut engaging member 1000 is illustrated in FIG. 10. In this embodiment, strut engaging member 1000 comprises a central portion 1002 that defines strut receiving recesses 1006 formed by flanges 1008. In some instances, flanges 1008 of strut engaging member 1000 may be arranged so as to resemble a dog bone and/or the letter "I".

Figures 11, 12:
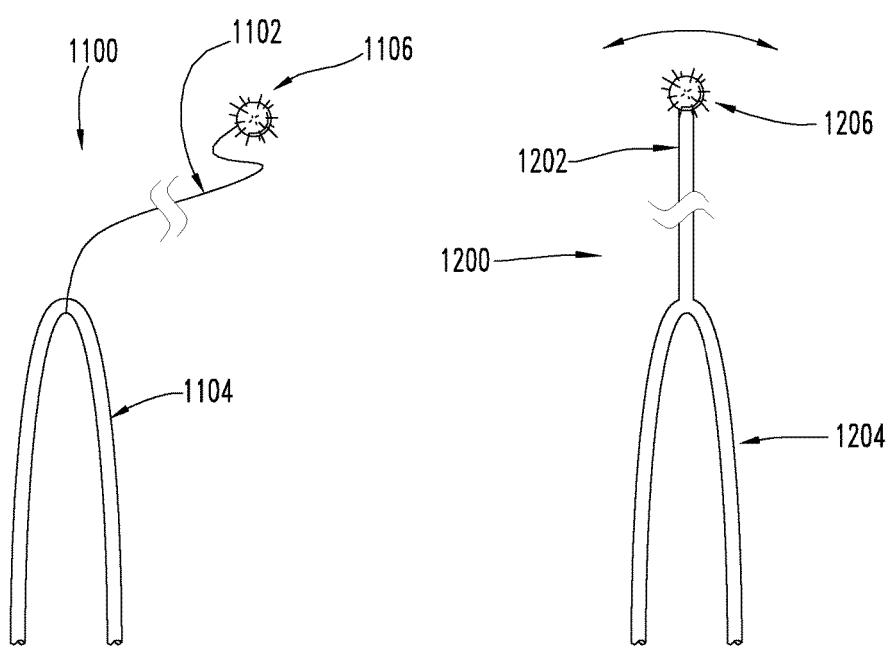
FIG. 11 is a front elevational view of an embodiment of a strut engaging member and elongate member.
FIG. 12 is front elevational view of another embodiment of a strut engaging member and elongate member.

FIG. 11 illustrates a device portion 1100 comprising an elongate member 1102 coupling loop 1104 with strut engaging member 1106. In some instances, elongate member 1102 is arranged so as to be wrappable around one or more struts, such as struts 406 of a vascular filter, and/or allow strut engaging member 1106 and elongate member 1102 to become tangled within struts of the vascular filter.

Similarly, in some embodiments such as that illustrated in FIG. 12, a device portion 1200 can comprise a resilient elongate member 1202 connecting loop 1204 with strut engaging member 1206. Advantageously, the resilient elongate member 1202 can allow for more precise control over the positioning of strut-engaging member 1206 within the vascular filter while still allowing strut-engaging member 1206 to deflect in one or more directions to engage with and/or wedge between struts of a vascular filter.

Figure 13:
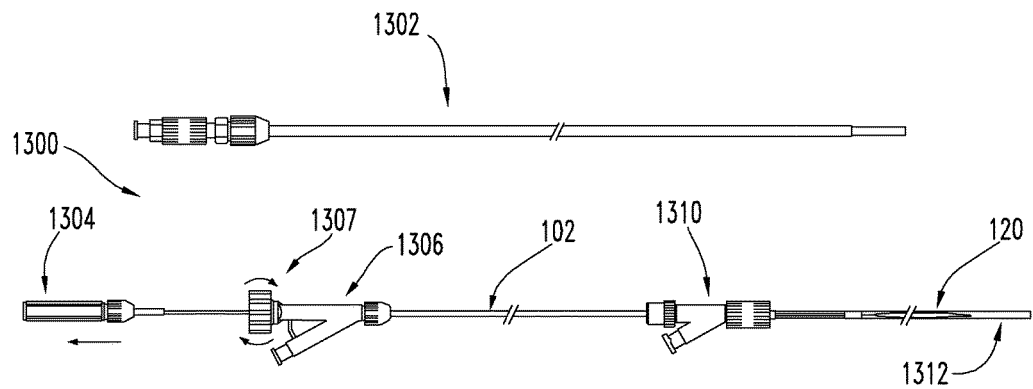
FIG. 13 is a top plan view of a retrieval system.

FIG. 13 illustrates a retrieval system comprising an exemplary retrieval device described above. The retrieval system comprises a retrieval loop system 1300 and a coaxial retrieval sheath system 1302. Retrieval loop system 1300 comprises a pin vise 1304 coupled to loop 120, a Y fitting 1306 coupled to catheter 102, and a side-arm adaptor 1310 coupled to an outer catheter 1312. Retrieval system, including retrieval loop system 1300 and coaxial retrieval sheath system 1302, may be sterily sealed in a package along with an introducer needle, wire guide, syringe, and/or a stopcock.

In a particular medical treatment, Y fitting 1306 is held and pin vise 1304 is pulled back so that loop 120 is covered by outer catheter 1312. Screw 1307 of Y fitting 1306 is tightened to keep loop 120 within outer catheter 1312 (illustrated in FIG. 13). The right jugular vein of a patient is punctured using the Seldinger technique. Although the right jugular vein approach is preferred, approach via the left jugular vein is possible.

A flush catheter can be positioned inferior to the filter 400 and a diagnostic vena cava performed. The flush catheter is then exchanged for the coaxial retrieval sheath system 1302 by advancing the coaxial retrieval sheath system 1302 over the wire guide. An inner coaxial catheter and the wire guide are removed once coaxial retrieval sheath system 1302 is in place. The position of the system can be verified by injection of contrast medium.

Figure 14A:
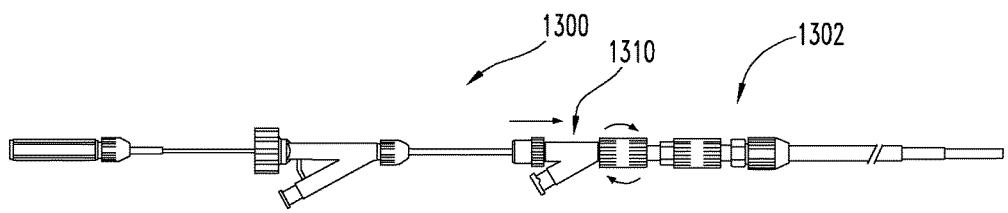
FIGS. 14a, 14b, 14c, 14d, 14e, and 14f illustrate schematic views of a retrieval system.
Figure 14B:
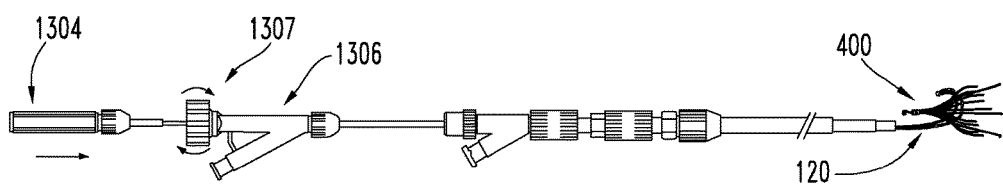

Retrieval loop system 1300 is introduced through coaxial retrieval sheath system 1302, advanced, and side-arm adaptor 1310 of the retrieval loop system 1300 connected to coaxial retrieval sheath system 1302. Side-arm adaptor 1310 can be tightened around outer catheter 1312 to prevent loss of blood (illustrated in FIG. 14*a*). Screw 1307 of Y fitting 1306 is then loosened to enable advancement of loop 120 inside catheter 102.

Figure 14C:
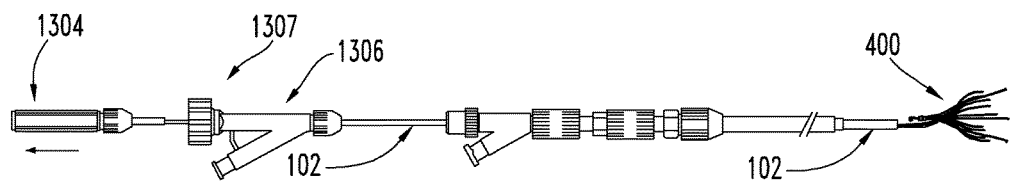
Figure 14D:
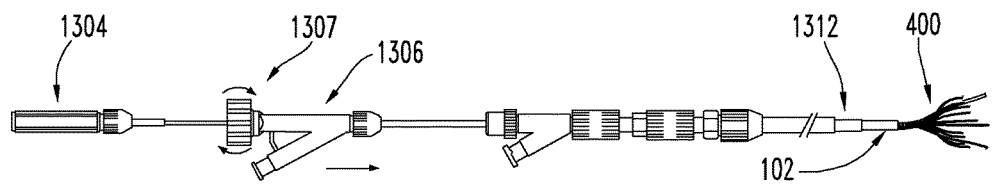

Whilst holding Y fitting 1306, pin vise 1304 is pushed forward and advanced until loop 120 has fully expanded inside the vena cava (FIG. 4*b*). Loop 120 is pulled back until strut-engaging member 140 is engaged with struts 460 of vascular filter 400 and loop 120 is under tension (FIG. 14*c*). Holding loop 120 steady with pin vise 1304, Y fitting 1306 is pushed with catheter 102 forward until catheter 102 aligns with vascular filter 400. Screw 1307 is then tightened (FIG. 14*d*).

Figure 14E:
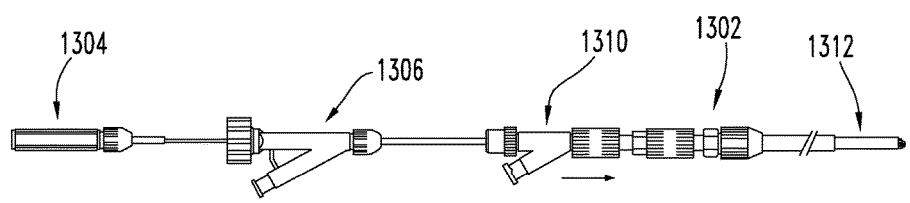
Figure 14F:
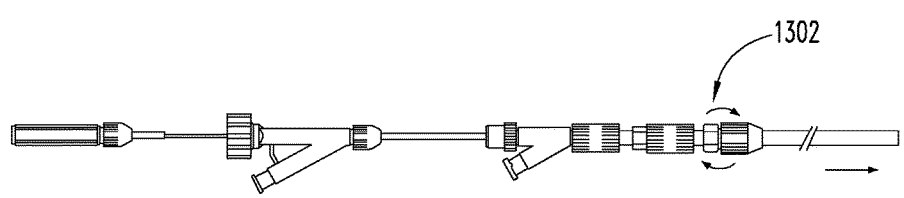

Holding pin vise 1304 and Y fitting 1306 steady, side-arm adaptor 1310 is advanced with the coaxial retrieval sheath system 1302, collapsing vascular filter 400 and disengaging struts 460 and barbs from the vessel wall 452 (FIG. 14*e*). When the tip of the coaxial retrieval sheath system 1302 is at the barbed ends of struts 460, the hub of coaxial retrieval sheath system 1302 is loosened and outer catheter 1312 advanced forward to cover the barbed portion of vascular filter 400, allowing the complete assembly to be retrieved (FIG. 14*f*).

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A device for retrieving a vascular filter having a plurality of struts from a body of a patient, comprising:
    a catheter defining a lumen;
    a loop deployable from and retractable into said lumen; and
    a strut engaging member fixedly coupled to said loop and defining first and second strut receiving recesses each arranged to receive at least one strut of the vascular filter;
    wherein said loop has a forward portion and a rearward portion and defines a loop opening when the loop is deployed from said lumen;
    wherein said forward portion exits the lumen before the rearward portion when the loop is deployed from the lumen;
    wherein said strut engaging member is fixedly coupled to said forward portion of said loop;
    wherein a first segment of said loop extends laterally of a first side of said strut engaging member and a second segment of said loop extends laterally of a second side of said strut engaging member;
    wherein when said loop is deployed from said lumen to an expanded configuration, said rearward portion defines a first plane and said forward portion of said loop curves out of said first plane; and
    wherein said first and second strut receiving recesses open away from said loop opening.

2. The device of claim 1, wherein:
    said loop is arranged to position said strut engaging member between struts of the vascular filter.

3. The device of claim 1, wherein:
    said loop is arranged to surround the vascular filter.

4. The device of claim 1, wherein:
    said first and second strut receiving recesses are arranged to wedge a portion of said strut engaging member between struts of the vascular filter.

5. The device of claim 1, wherein:
    said strut receiving recesses are defined by a plurality of elongate outward protrusions on said strut engaging member.

6. The device of claim 1, further comprising:
    an elongate member coupling said strut engaging member to said loop.

7. The device of claim 6, wherein:
    said elongate member is wrappable around at least one strut of the vascular filter.

8. The device of claim 1, wherein:
    an intermediate portion of said loop extends between said forward portion and said rearward portion; and
    wherein when said loop is deployed from said lumen to an expanded configuration said forward portion is positioned rearward of said intermediate portion.

9. A device for retrieving a vascular filter having a plurality of struts from a body of a patient, comprising:
    a catheter defining a lumen;
    a loop deployable from and retractable into said lumen; and
    an elongate member coupling a strut engaging member to said loop;

wherein said loop has a forward portion and a rearward portion;

wherein said forward portion exits the lumen before the rearward portion when the loop is deployed from the lumen;

wherein said strut engaging member is fixedly coupled to said forward portion of said loop;

wherein a first segment of said loop extends laterally of a first side of said strut engaging member and a second segment of said loop extends laterally of a second side of said strut engaging member; and wherein when said loop is deployed from said lumen to an expanded configuration said rearward portion defines a first plane and said forward portion of said loop curves out of said first plane and through an angle of about 180 degrees.

10. The device of claim 9, wherein:

said loop is arranged to position said strut engaging member between struts of the vascular filter.

11. The device of claim 9, wherein:

said elongate member is wrappable around a strut of the vascular filter.

12. The device of claim 11, wherein:

said strut engaging member is arranged to hook said elongate member.

13. A device for retrieving a vascular filter having a plurality of struts from a body of a patient, comprising:

a loop having a strut engaging member fixedly coupled thereto;

said loop arranged to contact the vascular filter along at least a plurality of discrete points and orient said strut engaging member for engagement with the struts of the vascular filter; and said strut engaging member arranged to engage struts of the vascular filter and couple at least a portion of the loop to the vascular filter;

wherein said loop has a forward portion and a rearward portion and said strut engaging member is fixedly coupled to said forward portion;

wherein a first segment of said loop extends rearwardly and laterally of a first side of said strut engaging member and a second segment of said loop extends rearwardly and laterally of a second side of said strut engaging member;

wherein said rearward portion of said loop defines a first plane and said forward portion of said loop curves out of said first plane and back toward said rearward portion so as to define a hook; and wherein said loop comprises a self-opening loop.

14. The device of claim 13, wherein:

said strut engaging member defines a strut receiving recess arranged to receive at least one strut of the vascular filter.

15. The device of claim 13, wherein:

said strut engaging member defines first and second strut receiving recesses each arranged to receive at least one strut of the vascular filter.

16. The device of claim 15, wherein:

said first and second strut receiving recesses are arranged to wedge at least a portion of said strut engaging member between struts of the vascular filter.

17. The device of claim 15, wherein:

said strut receiving recesses are defined by a plurality of elongate outward protrusions on said strut engaging member.

18. The device of claim 13, wherein:

said loop is arranged to surround the vascular filter.

19. The device of claim 13, further comprising:

an elongate member coupling said strut engaging member to said loop.

20. The device of claim 19, wherein:

said elongate member is wrappable around at least one strut of the vascular filter.

* * * * *